(12) United States Patent
Thomas

(10) Patent No.: US 10,172,724 B2
(45) Date of Patent: Jan. 8, 2019

(54) HARNESS FOR UPPER EXTREMITY BELOW-ELBOW PROSTHESIS

(71) Applicant: Mark Thomas, Phoenix, AZ (US)

(72) Inventor: Mark Thomas, Phoenix, AZ (US)

( * ) Notice: Subject to any disclaimer, the term of this patent is extended or adjusted under 35 U.S.C. 154(b) by 0 days.

(21) Appl. No.: 15/359,977

(22) Filed: Nov. 23, 2016

(65) Prior Publication Data

US 2018/0140442 A1 May 24, 2018

(51) Int. Cl.
*A61F 2/78* (2006.01)
*A61F 2/74* (2006.01)
*A61F 2/54* (2006.01)
*A61F 2/68* (2006.01)
*A61F 2/50* (2006.01)
*A61F 2/58* (2006.01)

(52) U.S. Cl.
CPC ............... *A61F 2/54* (2013.01); *A61F 2/68* (2013.01); *A61F 2/78* (2013.01); *A61F 2/582* (2013.01); *A61F 2002/5093* (2013.01); *A61F 2002/543* (2013.01); *A61F 2002/6872* (2013.01); *A61F 2002/7862* (2013.01)

(58) Field of Classification Search
CPC ...... A61F 2/54; A61F 2/76; A61F 2/78; A61F 2002/543; A61F 2002/7862; A61F 2002/6872; A61H 1/0274
See application file for complete search history.

(56) References Cited

U.S. PATENT DOCUMENTS

| 493,440 | A | * | 3/1893 | Selpho et al. | .......... A61F 2/588 623/63 |
| 1,206,753 | A | * | 11/1916 | Minzey | .................... A61F 2/588 623/61 |
| 1,323,671 | A | * | 12/1919 | Desmore | .................... A61F 2/54 623/63 |
| 1,408,157 | A | * | 2/1922 | Armstrong | ................ A61F 2/54 623/59 |
| 1,464,842 | A | * | 8/1923 | Burgan | ...................... A61F 2/54 623/63 |
| 2,812,961 | A | * | 11/1957 | Brown | ..................... A61F 2/582 403/93 |
| 5,163,966 | A | | 11/1992 | Norton et al. | |
| 5,800,572 | A | | 9/1998 | Loveall | |
| 5,888,235 | A | | 3/1999 | Jacobsen et al. | |
| 7,967,869 | B2 | | 6/2011 | Schulman et al. | |

(Continued)

OTHER PUBLICATIONS

Owen, Jen. Enabling the Future. Oct. 1, 2015.*

(Continued)

*Primary Examiner* — Thomas J Sweet
*Assistant Examiner* — Christie Bahena
(74) *Attorney, Agent, or Firm* — Global Intellectual Property Agency, LLC; Daniel Boudwin

(57) ABSTRACT

A harness for an upper extremity below-elbow prosthesis. The harness includes a humeral cuff having medial and lateral pivot arms configured to removably attach to the socket of a below-elbow prosthesis. The humeral cuff enables a user to suspend the prosthesis without the need of a shoulder strap/harness or body harness. A cable system is affixed to the pivot arms and includes a wheel coupling the pivot arms to the control arm of a hook of the below-elbow prosthesis, thereby enabling users to operate the hook by simple flexion and extension of their arm.

14 Claims, 6 Drawing Sheets

(56) References Cited

U.S. PATENT DOCUMENTS

| | | | |
|---|---|---|---|
| 8,414,658 B2 | 4/2013 | Johnson et al. | |
| 2007/0250179 A1* | 10/2007 | Latour | A61F 2/54 606/60 |
| 2013/0090743 A1* | 4/2013 | Latour | A61F 2/54 623/58 |

OTHER PUBLICATIONS

Kay, Hector. The Munster-Type Below-Elbow Socket, a Fabrication Technique. The oandp library. 1965.*
Richter, Henry. Full Cuff Control. Orthotics and Prosthetics, vol. 40, No. 4, p. 28-34. 1987.*
Toughware. ITAL: Fitting and Use. Catalog. 2013.*

* cited by examiner

HARNESS FOR UPPER EXTREMITY BELOW-ELBOW PROSTHESIS

BACKGROUND OF THE INVENTION

The present invention relates to upper extremity below-elbow prostheses. More specifically, the present invention relates to a harness for an upper extremity below-elbow prosthesis capable of suspending a below-elbow prosthesis and facilitating its operation without the need of a shoulder strap/harness or body harness.

The majority of below-elbow amputees utilize mechanical or body-powered prosthesis that are suspended on an amputee's body via a harness that is fastened around the amputee's shoulder or upper torso. The prosthesis is controlled by upper body movements that utilize a cable connected to the harness at one end, and to a mechanical hand, hook, or elbow at the other end. Although, these harness systems provide ways in which an amputee may employ a prosthesis, they generally lack the range of motion necessary for adequate flexion and extension of a user's arm with the prosthesis. Moreover, when opening the hook of the prosthesis, these systems often require that the amputee use more physical upper body movement and strength, which can be onerous to an amputee utilizing the prosthesis for extended periods of time. Further, these shoulder harness systems are overall uncomfortable in that they give a user a feeling of confinement and are cumbersome to wear whether over or underneath a user's shirt. Therefore, there is a need in the art for an improved prosthesis harness configured to be attached to the socket of an upper extremity below-elbow prosthesis, which eliminates the need for a shoulder or body harness and facilities full range of motion of the prosthesis.

The use of harnesses for upper extremity below-elbow prosthesis are known in the prior art. More specifically, harnesses heretofore devised and utilized are known to consist basically of familiar, expected and obvious structural configurations, notwithstanding the myriad of designs encompassed by the crowded prior art which have been developed for the fulfillment of countless objectives and requirements.

While these devices fulfill their respective, particular objectives and requirements, the aforementioned patents do not disclose a harness for an upper extremity below-elbow prosthesis having a humeral cuff, medial and lateral pivot arms having upper and lower members pivotally attached to one another; a cable system having a first cable, a second cable, a medial cable anchor, a lateral cable anchor, and a wheel having a central cable anchor.

In these respects, the harness according to the present invention substantially departs from the conventional concepts and designs of the prior art, and in so doing provides an apparatus primarily developed for the purpose of providing a harness for an upper extremity below-elbow prosthesis that is capable of attaching to the socket of the prosthesis and suspending it for use, without the need of a shoulder or body harness, and which facilitates full range of flexion and extension of the prosthesis.

SUMMARY OF THE INVENTION

In view of the foregoing disadvantages inherent in the known types of harnesses now present in the prior art, the present invention provides a harness for an upper extremity below-elbow prosthesis wherein the same can be utilized for providing convenience for the user when utilizing below-elbow prosthesis. The present system comprises a humeral cuff configured to slidably receive an arm of an upper extremity therethrough, a medial pivot arm having an upper member and a lower member, the upper member and the lower member being pivotally connected, a lateral pivot arm having an upper member and a lower member, the upper member and the lower member being pivotally connected, wherein the upper member of the medial pivot arm is removably affixed to a medial aspect of the humeral cuff, wherein the upper member of the lateral pivot arm is removably affixed to a lateral aspect of the humeral cuff, a cable system, comprising, a first cable having a medial end and a lateral end, a second cable having a first end and a second end, a medial cable anchor pivotally affixed to the upper member of the medial pivot arm, the medial cable anchor being configured to slidably receive the medial end of the first cable, a lateral cable anchor pivotally affixed to the upper member of the lateral pivot arm, the lateral cable anchor being configured to slidably receive the lateral end of the first cable, a wheel configured to receive the first cable therearound, a central cable anchor affixed to the wheel, the central cable anchor configured to receive the first end of the second cable, wherein the second end of the second cable is configured to removably attach to a control arm of a hook of a below-elbow prosthesis, wherein the cable system exerts a tension on the control arm of the hook of the below-elbow prosthesis as the prosthesis is extended from a flexed position, such that the harness automatically opens the hook of the below-elbow prosthesis when extended, and wherein the wheel is configured to enable the cable system to exert equal tension on both the medial and lateral pivot arms when opening a rotate hook of a below-elbow prosthesis.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
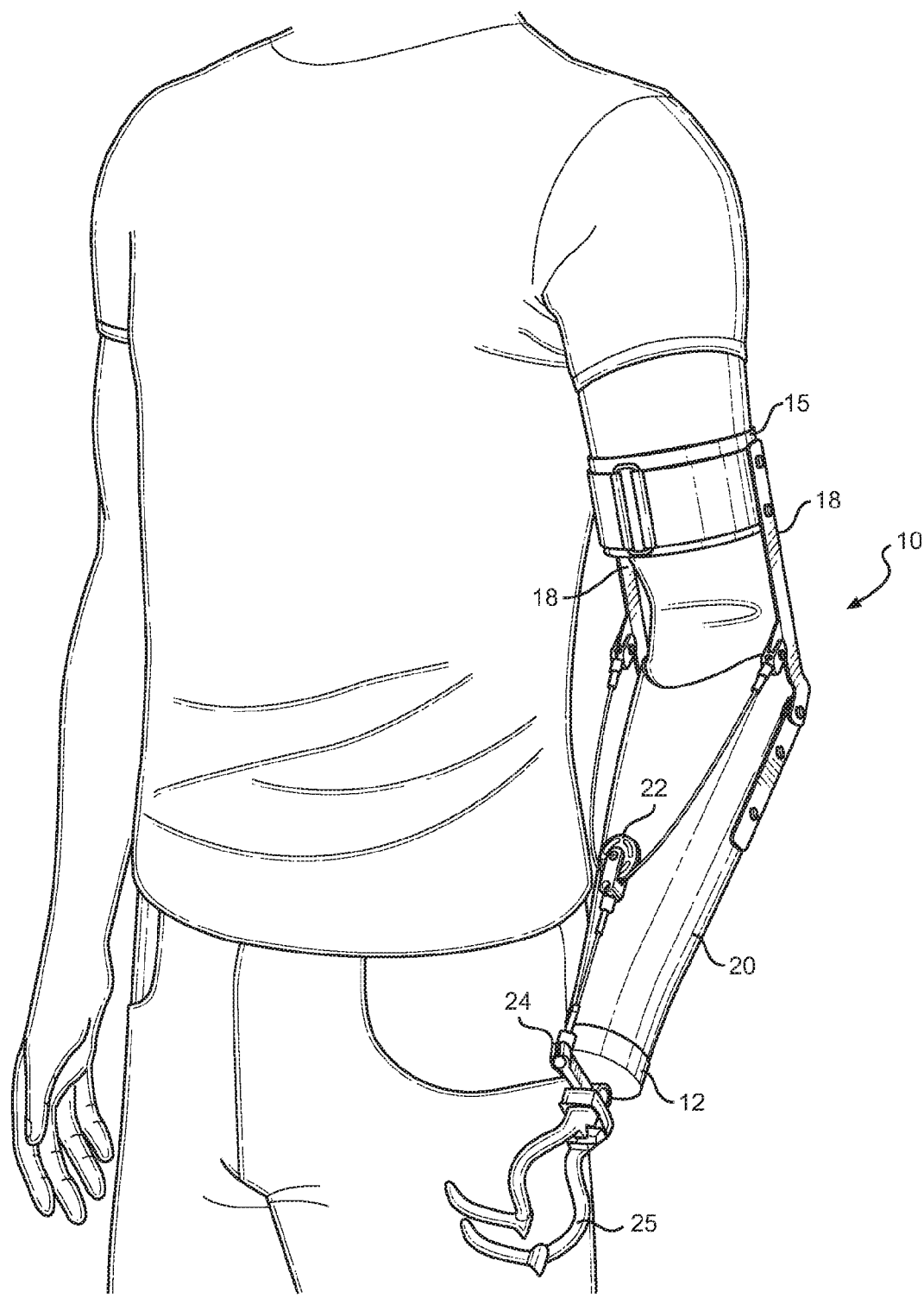
FIG. 1 shows a perspective view of the harness mounted onto an upper extremity below-elbow prosthesis.

Reference is made herein to the attached drawings. Like reference numerals are used throughout the drawings to depict like or similar elements of the harness for upper extremity below-elbow prosthesis. The figures are intended for representative purposes only and should not be considered to be limiting in any respect.

Referring now to FIG. 1, there is shown a perspective view of the harness mounted onto an upper extremity below-elbow prosthesis. The present invention comprises a harness 10 for an upper extremity below-elbow prosthesis 12. The harness 10 comprises a humeral cuff 15 configured to receive the arm of an upper extremity, pivot arms 18 configured to attach to the forearm area of a socket 20 of the below-elbow prosthesis 12, and a cable system 22 configured to couple the pivot arms 18 and a control arm 24 of a hook of the below-elbow prosthesis 12 in order to facilitate the flexion and extension of the prosthesis 12 and the operation of the hook.

Figure 2:
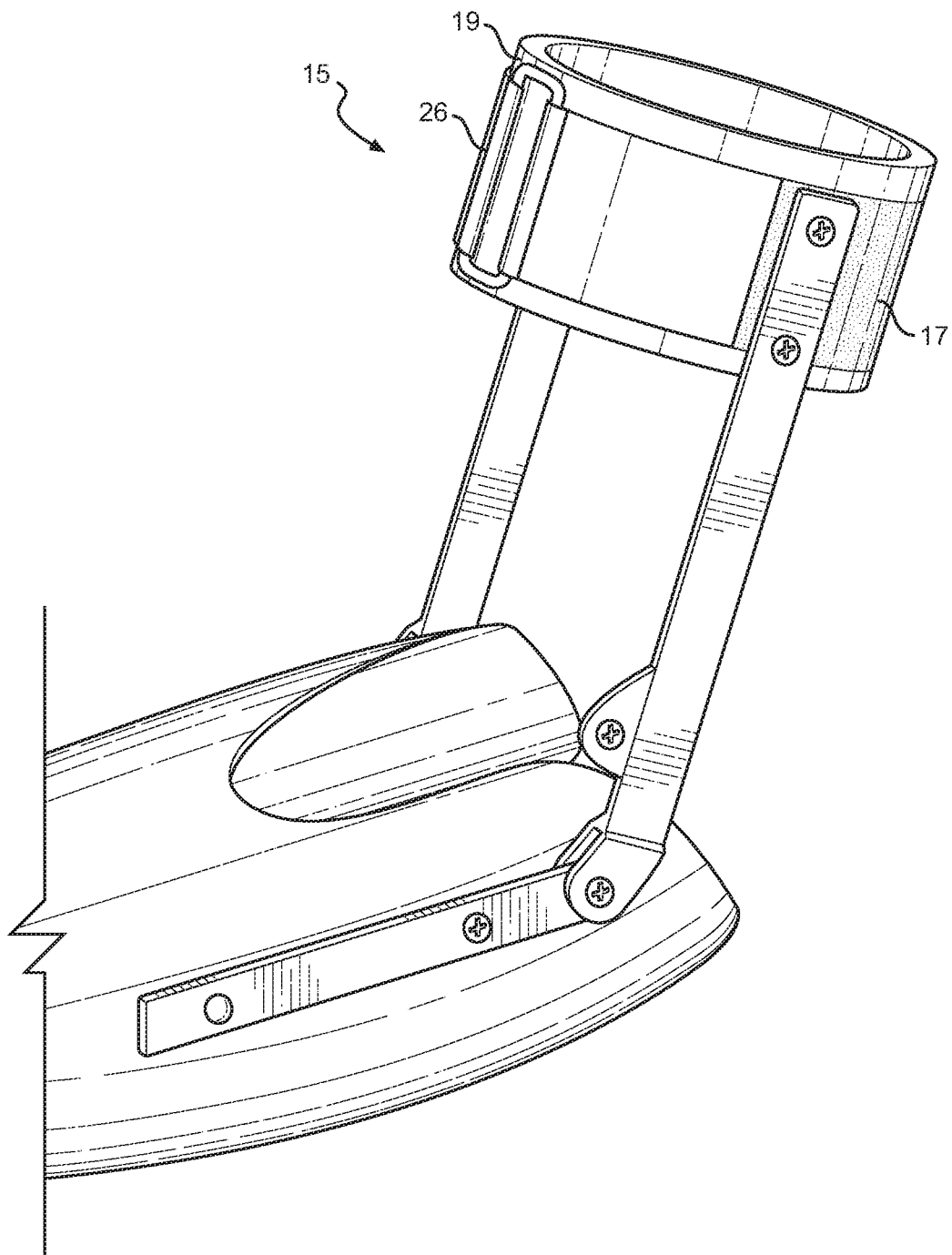
FIG. 2 shows a close-up view of the humeral cuff of the harness.

Referring now to FIG. 2, there is shown a close up view of the humeral cuff of the harness. The humeral cuff 15 is configured to receive an upper arm therethrough. The humeral cuff 15 comprises an arm support 17 constructed of durable material, such as carbon fiber, steel, aluminum, titanium, or any combination thereof, that is configured to be molded into a desired size to fit users having differently sized arms. The arm support 17 provides support to the harness and user when suspending a below-elbow prosthesis therefrom. In one embodiment, the arm support 17 comprises a semicircular band of carbon fiber positioned on the back half of the humeral cuff 15. The humeral cuff 15 further comprises an arm pad 19 disposed around an interior thereof. The arm pad 19 comprises a cushioned material for providing a padded surface on which a user's arm may make contact to provide comfort. In one embodiment, the arm pad 19 comprises a leather band or strap. In another embodiment, the arm pad 19 comprises a foam band. The humeral cuff 15 further comprises a fastener 26 that is adjustable and enables the humeral cuff 15 to be tightened and adjusted around an arm as desired. In one embodiment, the fastener 26 comprises an adjustable strap having a hook-and-loop fastener and a buckle for pulling the strap therethrough and adjusting it to tighten or loosen the humeral cuff 15. In another embodiment, the fastener comprises a ratcheting strap.

Figure 3:
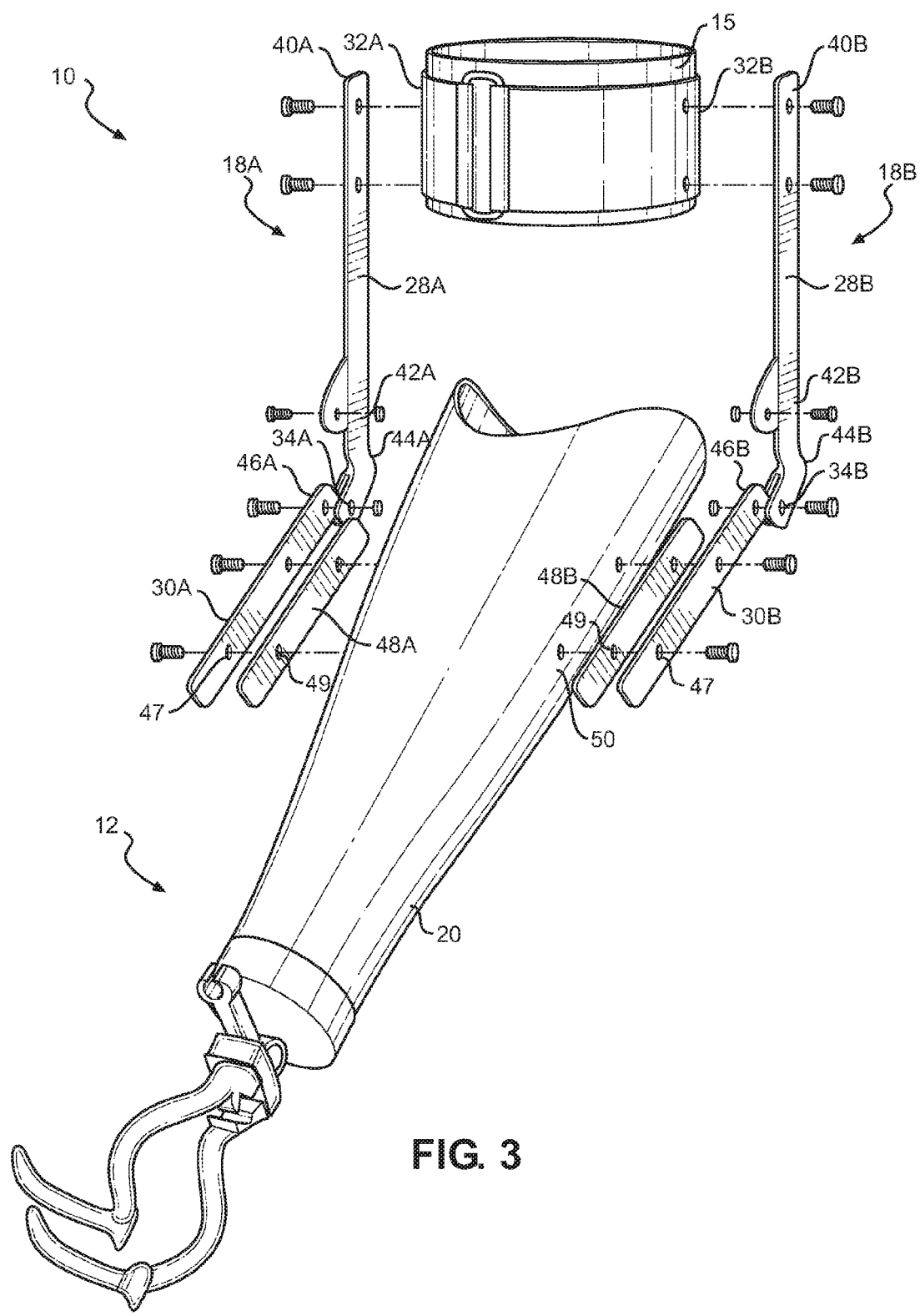
FIG. 3 shows an exploded view of the pivot arms of the harness.

Referring now to FIG. 3, there is shown an exploded view of the pivot arms of the harness. The harness 10 further comprises a medial pivot arm 18A and a lateral pivot arm 18B. The medial pivot arm 18A comprises an upper member 28A and a lower member 30A and the lateral pivot arm 18B comprises an upper member 28B and a lower member 30B. The medial and lateral upper members 28A, 28B are elongated planar plates, each having a first end 40A, 40B and a second end 42A, 42B. The medial first end 40A and the lateral first end 40B are removably affixed to the medial aspect 32A and lateral aspect 32B, respectively, of the humeral cuff 15. The second ends 42A, 42B each comprise an elbow portion 44A, 44B pivotally affixed to the corresponding lower member 30A, 30B. In an alternative embodiment of the present harness, the medial first end 40A and the lateral first end 40B are integrally affixed to the medial and lateral aspects 32A, 32B, respectively, of the humeral cuff 15. In another embodiment, the first ends 40A, 40B of the upper members 28A, 28B comprise apertures configured to receive fasteners therethrough for fastening the upper members 28A and 28B to the humeral cuff 15.

The medial and lateral lower members 30A, 30B also comprise elongated planar plates, wherein the plates are configured to be attached to the forearm portion 50 of a socket 20 of a below-elbow prosthesis 12. Each of the medial and lateral lower member 30A, 30B comprises a pivot end 46A, 46B that are configured to be pivotally attached to the corresponding elbow portion 44A, 44B of the upper members 28A, 28B via a hinge 34A, 34B. In one embodiment, the elbow portions 44A, 44B and the pivot ends 46A, 46B are connected via a pivot hinge. In another embodiment, the elbow portions 44A, 44B and pivot ends 46A, 46B are connected via a polycentric hinge.

The harness 10 further comprises a medial mounting bracket 48A and a lateral mounting bracket 48B having a plurality of apertures 49 for receiving fasteners therethrough for mounting the lower members 30A, 30B onto the socket 20. In one embodiment, the medial and lateral mounting brackets 48A, 48B are configured to be integrated into the forearm socket 20 via lamination. The medial and lateral mounting brackets 48A and 48B are mountable onto the socket 20 and provide an intermediary bracket on which to attach and mount the corresponding lower member 30A, 30B onto the socket 20.

The positioning of the upper members 28A, 28B relative to the lower members 30A, 30B is adjustable so that the present harness can be adjusted as a user grows or for different users. In the depicted embodiment of the harness, the elbow portions 44A, 44B of the upper members 28A, 28B are attachable to one of multiple different apertures 47 disposed along the length of each of the lower members 30A, 30B. In this way, the position of pivot arms 18A, 18B may be adjusted along the forearm socket 20, thereby adjusting the position of the humeral cuff 15 relative to the forearm socket 20. The medial and lateral mounting brackets 48A, 48B further serve as spacers for spacing the hinges 34A, 34B and the socket 20 of the below-elbow prosthesis, thereby facilitating frictionless movement in between the hinges 34A, 34B and the socket 20.

Figure 4:
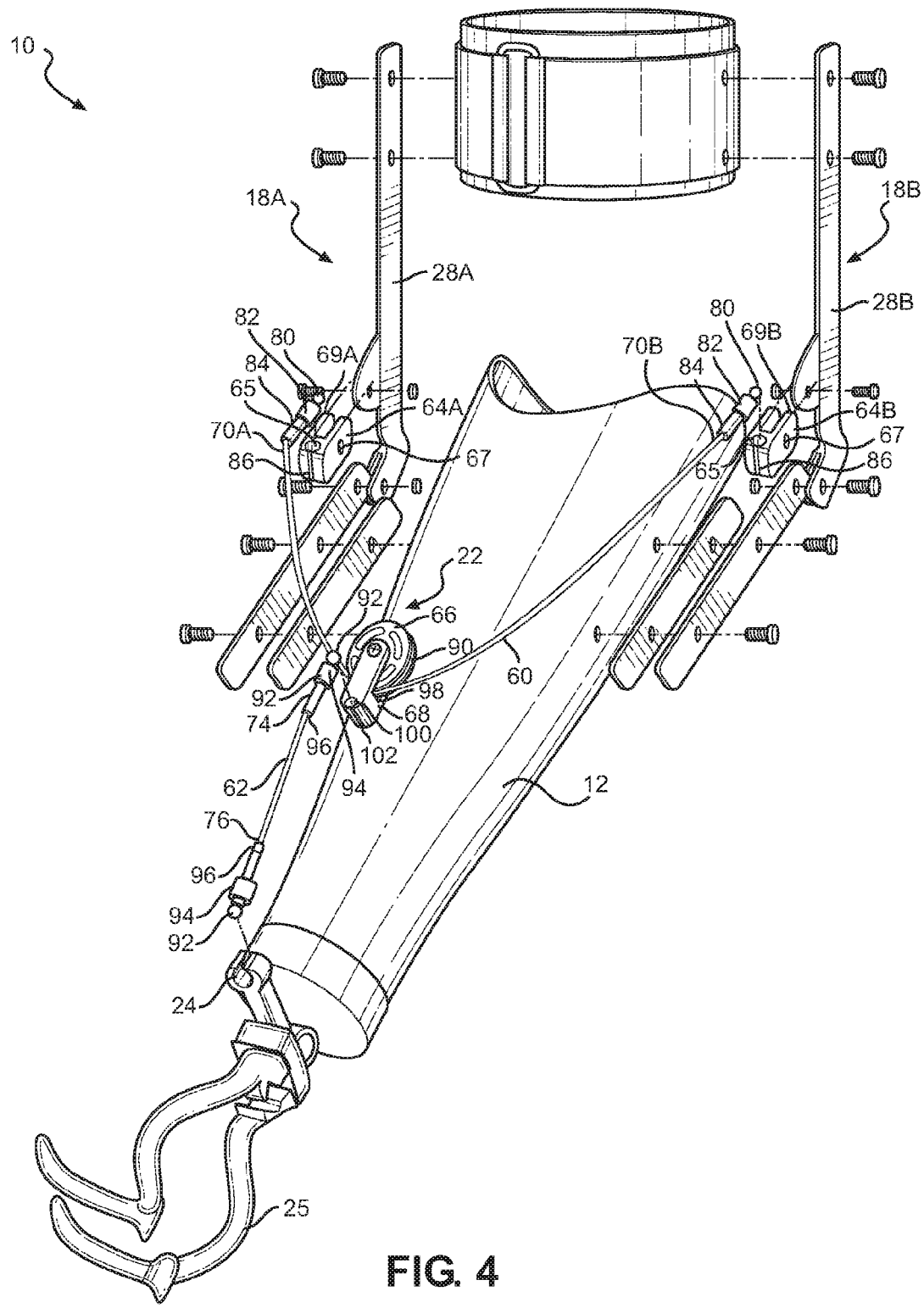
FIG. 4 shows an exploded view of the cable system of the harness.

Referring now to FIG. 4, there is shown an exploded view of the cable system of the harness. The cable system 22 of the harness 10 comprises a first cable 60, a second cable 62, a medial cable anchor 64A, a lateral cable anchor 64B, and a wheel 66 having a central anchor 68 affixed thereto. The first cable 60 comprises a medial end 70A and a lateral end 70B that each include a swivel ball 80, a grommet 82, and a ferrule 84. The second cable 62 comprises a first end 74 and a second end 76 that likewise each include a swivel ball 92, a grommet 94, and a ferrule 96. The first and second cable 60, 62 are fixed in length, but can be constructed to have different lengths to accommodate users of different sizes.

Each of the medial and lateral cable anchors 64A, 64B comprises a race 65 and an aperture 67. The cable anchors 64A, 64B are fastened to the pivot arms 18A, 18B by a fastener securable through the apertures 67. The races 65 include a slot 86 sized to slidably receive the swivel ball 80 disposed at the ends of the ends 70A, 70B of the first cable 60. The medial cable anchor 64A is pivotally connected to the upper member 28A of the medial pivot arm 18A via a medial cable anchor hinge 69A. The lateral cable anchor 64B is pivotally connected to the upper member 28B of the lateral pivot arm 18B via a lateral cable anchor hinge 69B. In one embodiment, the medial and lateral cable anchor hinges 69A, 69B are pivot hinges. In another embodiment, the medial and lateral cable anchor hinges 69A, 69B are polycentric hinges. The lateral cable anchor and the medial cable anchor are each disposed at an equivalent linear distance from humeral cuff, such that force is evenly exerted upon each of the lateral cable anchor and the medial cable anchor.

The swivel ball 80 of the medial end 70A is rotatably retained within the race 65 of the medial cable anchor 64A, creating a coupling that allows the medial end 70A to rotate relative to the medial cable anchor 64A. The swivel ball 80 of the lateral end 70B is rotatably retained within the race 65 of the lateral cable anchor 64B, creating a coupling that allows the medial end 70B to rotate relative to the lateral cable anchor 64A. The grommets 82 of the medial and lateral ends 70A, 70B are reinforcements configured to secure the swivel balls 80 in the races 65 and prevent the swivel balls 80 from slipping therefrom. When the swivel balls 80 are positioned inside of the races 65, the grommets 82 secure the ends 70A, 70B of the cable 60 inside of the slots 86 thereby preventing the swivel balls 80 from slipping from the races 65. In one embodiment, the grommets 82 are rubber grommets. The ferrules 84 of the medial and lateral ends 70A, 70B of the first cable 60 reinforce the medial and lateral ends 70A, 70B by strengthening the coupling of the swivel balls 80 and the medial and lateral ends 70A, 70B.

The wheel 66 operably couples the first cable 60 and the cable anchors 64A, 64B to the central cable anchor 68, which in turn couples the second cable 62 to a control arm 24 of the hook of a below-elbow prosthesis 12. The wheel 66 comprises a tread 90 configured to receive and retain the first cable 60 thereon, thereby suspending the first cable 60 around the wheel 66. The central cable anchor 68 is affixed to the wheel 66 and includes an aperture 98, which is configured to receive the first cable 60 therethrough.

The central cable anchor 68 also comprises a central race 100 having a circular receptacle sized to slidably receive a swivel ball therein and a slot 102 sized to receive the first end 74 of the second cable 62 therethrough. The swivel ball 92 of the first end 74 of the second cable 62 is rotatably retained within the central race 100 of the central cable anchor 68, creating a coupling that allows the first end 74 to rotate relative to the central cable anchor 68. The swivel ball 92 of the second end 76 of the second cable 62 is capable of being rotatably received by the control arm 24 of the hook of the below-elbow prosthesis 12, creating a coupling that allows the second end 76 to rotate relative to the control arm 24.

The grommets 94 of the first and second ends 74, 76 are reinforcements configured to secure the swivel balls 92 in the receptacle of the central race 100 and the control arm 24 of the prosthesis 12 and prevent the swivel balls 92 from sliding thereout. When the swivel balls 92 are positioned inside of the central race 100 and the control arm 24, the grommets 94 secure the ends 74, 76 of the cable 60 inside of the slot 102 and the control arm 24 respectively, thereby preventing the swivel balls 92 from slipping therefrom. In one embodiment, the grommets 94 are rubber grommets. The ferrules 96 of the first and second ends 74, 76 of the second cable 62 reinforce the first and second ends 74, 76 by strengthening the coupling of the swivel balls 92 and the first and second ends 74, 76.

Figure 5A:
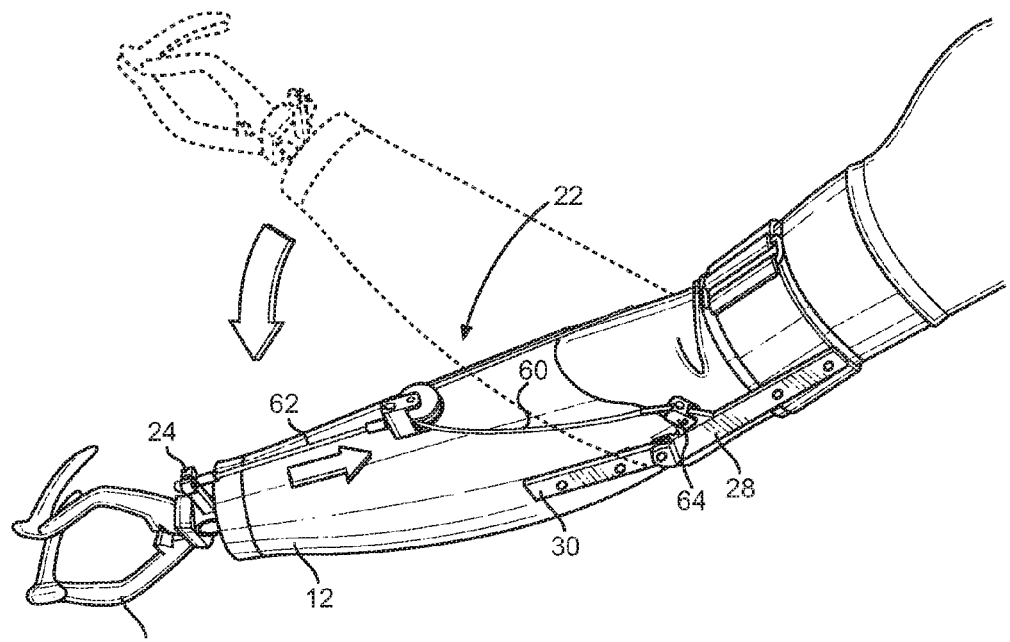
FIG. 5A shows a view of the harness in an extended position.
Figure 5B:
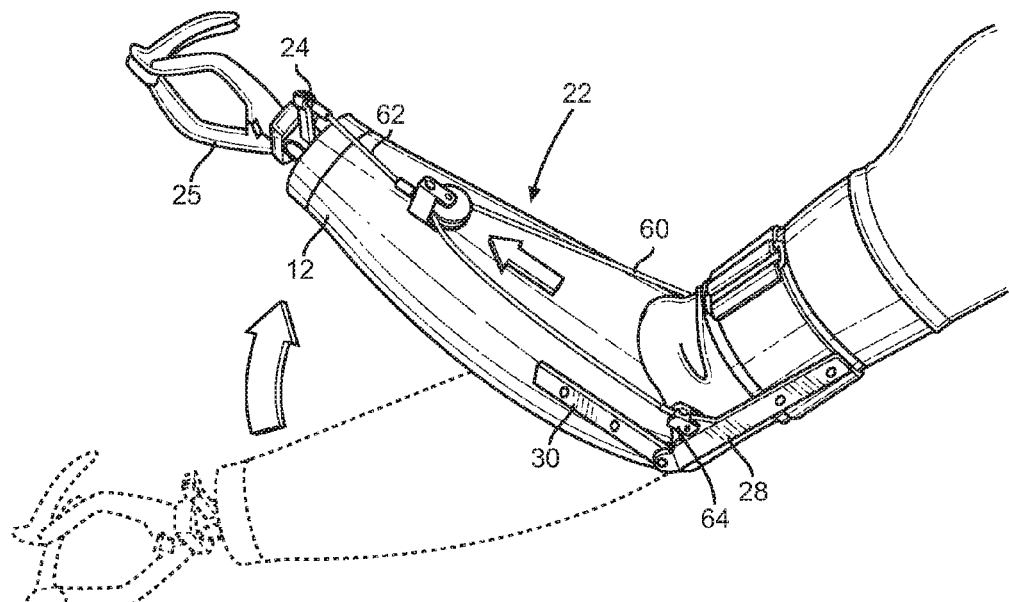
FIG. 5B shows a view of the harness in a flexed position.

Referring now to FIGS. 5A and 5B, there are shown views of the harness being flexed and extended. The cable system 22 operates to enable a user to move a suspended below-elbow prosthesis 12 from a flexed position, as shown in FIG. 5B, into an extended position, as shown in FIG. 5A, and open the hook of the prosthesis 12 as the prosthesis 12 is moved into the extended position. Due to the first and second cables 60, 62 being of fixed lengths and the medial and lateral cable anchors 64 being disposed above a user's elbows when affixed to a below-elbow prosthesis 12, extension of the below-elbow prosthesis 12 exerts tension on the control arm 24 of the hook 25, which in turn opens the hook 25. Specifically, the first cable 60 and the second cable 62 work together to exert a tension on the control arm 24. In operation, when the cable system 22 is in a flexed position, it exerts no tension on the control arm 24. However, when the below-elbow prosthesis 12 is extended, the further the prosthesis 12 is extended, the greater the tension exerted on the control arm 24. This is due to the increasing distance in between the cable anchors 64 on the upper members 28 and the control arm 24 and the increasing angle of the lower member of the harness relative to the upper member of the harness. The greater the distance and angle, the greater the tension the cable system 22 exerts on the control arm 24. Furthermore, the length of the first and second cables 60, 62 are sized to enable the harness 10 to extend such that the upper member 28 is situated at a 180-degree angle relative to the lower member 30, thereby providing a user full range of motion of the prosthesis 12 when utilizing the harness. Moreover, when the upper member 28 is situated at a 180-degree angle relative to the lower member 30, the distance in between the cable anchors 64 and the control arm 24 is maximized thereby completely opening the hook 25 and maximizing its grasping capacity.

Figure 6:
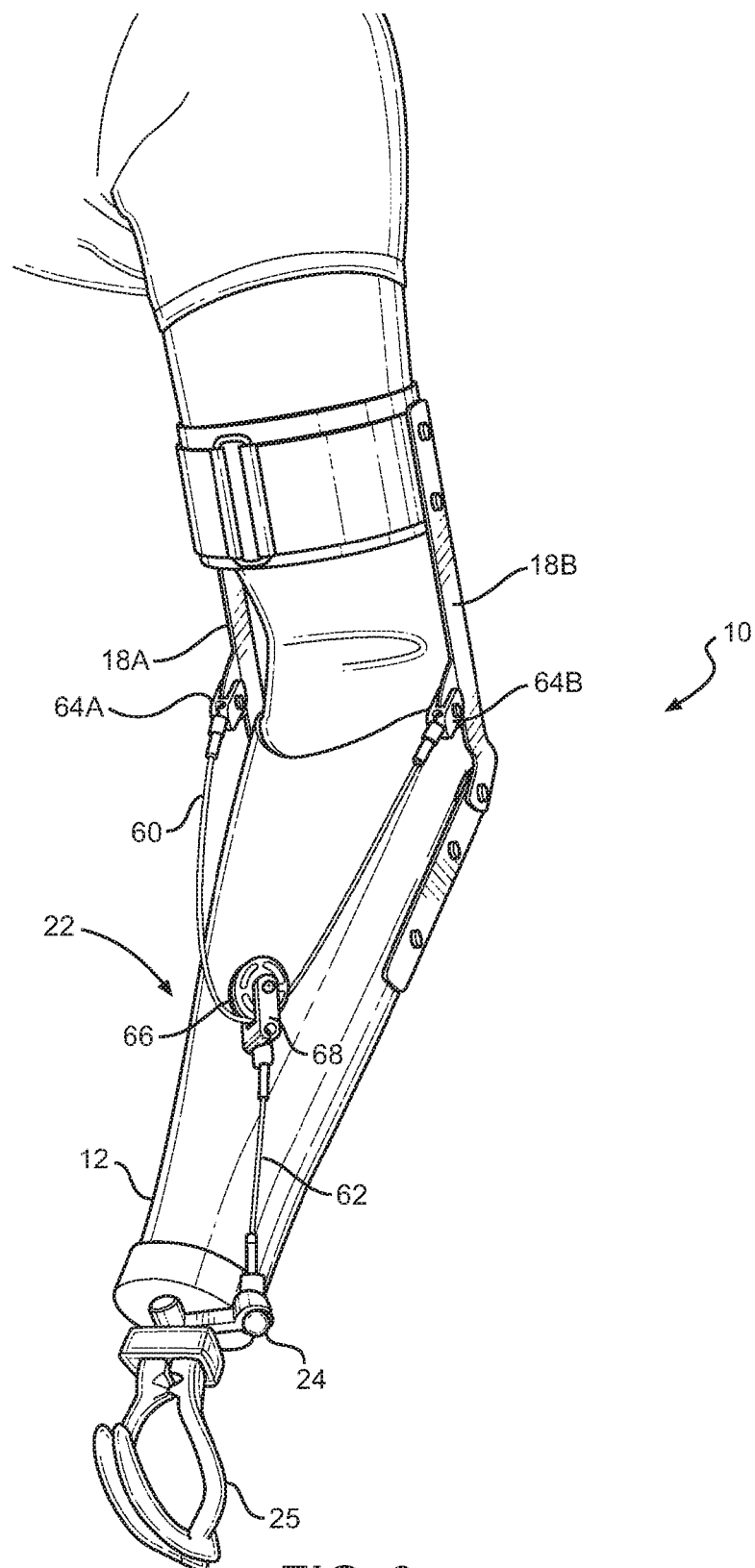
FIG. 6 shows a view of a rotated hook on a prosthesis and the wheel operating to provide equal tension to the medial and lateral pivots arms of the harness.

Referring now to FIG. 6, there is shown a view of a rotated hook on a prosthesis and the wheel operating to provide equal tension to the medial and lateral pivots arms of the harness. In conventional usage of upper extremity below-elbow prosthesis, users manually rotate the hook 25 of a prosthesis 12 to change the hook's 25 orientation and facilitate the grasping of certain items and affect their maneuverability therewith. When the hook 25 is rotated, the position of the control arm 24 changes relative to the central cable anchor 68. For example, when the hook 25 is rotated 90 degrees towards to the lateral pivot arm 18B, the control arm 24, as shown in FIG. 6, moves into a perpendicular orientation relative to the lateral pivot arm 18B. Since the cable system 22 is attached to the control arm 24, the cable system 22 rotates with the control arm 24. When the control arm 24 rotates, the second cable 62 moves the wheel 66 via the central cable anchor 68 along the first cable 60 towards the lateral cable anchor 64B to stabilize the tension exerted by the second cable 62 on the first cable 60.

The movement of the wheel 66 along the first cable 60 towards the pivot arm to which the hook 25 has been rotated alters the point along the first cable 60 at which the second cable 62 exerts tension. Enabling the second cable 62 to exert a tension along different points on the first cable 60 enables the cable system 22 to evenly distribute the tension exerted on both the first and second cable anchors 64A, 64B via the first cable 60. The equal distribution of tension on pivot arms 18, 18B is preferable because an unequal distribution of tension to either pivot arm causes the prosthesis 12 to rotate on a user's extremity when extending the arm to open the hook 25, thereby rendering the prosthesis 12 inoperable and causing discomfort to the user.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A cuff for below-elbow prosthesis, comprising:
   a humeral cuff configured to slidably receive an arm of an upper extremity therethrough;
   a medial pivot arm having an upper member and a lower member, the upper member and the lower member being pivotally connected;
   a lateral pivot arm having an upper member and a lower member, the upper member and the lower member being pivotally connected;
   wherein the upper member of the medical pivot arm is removably affixed to a medial aspect of the humeral cuff;
   wherein the upper member of the lateral pivot arm is removably affixed to a lateral aspect of the humeral cuff;
   a cable system, comprising:
      a first cable having a medial end and a lateral end;
      a second cable having a first end and a second end;
      a medial cable anchor pivotally affixed to the upper member of the medial pivot arm, the medial cable anchor being configured to slidably receive the medial end of the first cable;
      a lateral cable anchor pivotally affixed to the upper member of the lateral pivot arm, the lateral cable anchor being configured to slidably receive the lateral end of the first cable;
      wherein the lateral cable anchor and the medial cable anchor are each disposed at an equivalent linear distance from the humeral cuff;
      a wheel configured to receive the first cable therearound;
      a central cable anchor affixed to the wheel, the central cable anchor configured to receive the first end of a second cable;
      wherein the second end of the second cable is configured to removably attach to a control arm of a hook of a below-elbow prosthesis;
      wherein the hook is biased in a closed position;
   wherein the cable system is operably connected to the control arm of the hook wherein variations in tension exerted upon the control arm resulting from movement of the prosthesis between a flexed position and an extended position will cause the hook to be closed when moved into the flexed position and opened when moved into the extended position;
   wherein the wheel is configured to enable the cable system to exert equal tension on both the medial and lateral pivot arms when opening the hook of the below-elbow prosthesis.

2. The cuff for below-elbow prosthesis of claim 1, further comprising medial and lateral mounting brackets, wherein the medial and lateral brackets are configured to be affixed to a below-elbow prosthesis and receive the medial and lateral members, respectively.

3. The cuff for below-elbow prosthesis of claim 2, wherein the medial and lateral mounting brackets comprise a plurality of apertures configured to receive fasteners therethrough.

4. The cuff for below-elbow prosthesis of claim 1, wherein the humeral cuff comprises:
   a semi-circular arm support, wherein the semi-circular arm support is disposed on a rear end of the humeral cuff;
   an arm pad disposed around an interior of the humeral cuff; and
   a fastener having an adjusting strap configured to tighten the humeral cuff around an arm and fasten the humeral cuff thereto.

5. The cuff for below-elbow prosthesis of claim 4, wherein the arm support is constructed of a durable material selected from the group consisting of carbon fiber, steel, aluminum, and titanium.

6. The cuff for below-elbow prosthesis of claim 1, wherein the medial and lateral cable anchors each comprise a race sized to receive a swivel ball therein and a slot configured to slidably receive an end of the first cable therethrough.

7. The cuff for below-elbow prosthesis of claim 6, wherein the medial and lateral ends of the first cable each comprise a swivel ball configured to slidably engage with the races of the medial and lateral cable anchors, respectively.

8. The cuff for below-elbow prosthesis of claim 7, wherein the medial and lateral ends of the first cable further comprise a rubber grommet and a ferrule.

9. The cuff for below-elbow prosthesis of claim 1, wherein the central cable anchor comprises a race sized to receive a swivel ball therein and a slot configured to slidably receive an end of a cable therethrough.

10. The cuff for below-elbow prosthesis of claim 9, wherein the first and second ends of the second cable each comprise a swivel ball, wherein the swivel ball of the first end is configured to slidably engage the race of the central cable anchor and the swivel ball of the second end is configured to slidably engage with a control arm of a hook of a below-elbow prosthesis.

11. The cuff for below-elbow prosthesis of claim 10, wherein the first and second ends of the second cable further comprise a rubber grommet and a ferrule.

12. The cuff for below-elbow prosthesis of claim 1, wherein the lower members of the medial and lateral pivots arms comprise one or more apertures for receiving a fastener therethrough.

13. The cuff for below-elbow prosthesis of claim 1, wherein the upper member and the lower members of the medial and lateral pivot arms are pivotally connected via a pivot hinge.

14. The cuff for below-elbow prosthesis of claim 1, wherein the medial and lateral cable anchors are pivotally connected to the medial and lateral upper members, respectively, via a pivot hinge.

* * * * *